(12) United States Patent  (10) Patent No.: US 7,934,912 B2
Voltenburg, Jr. et al.  (45) Date of Patent: May 3, 2011

(54) PERISTALTIC PUMP ASSEMBLY WITH CASSETTE AND MOUNTING PIN ARRANGEMENT

(75) Inventors: Robert R. Voltenburg, Jr., Davison, MI (US); Loren M. Thompson, Lapeer, MI (US)

(73) Assignee: Curlin Medical Inc, East Aurora, NY (US)

( * ) Notice: Subject to any disclaimer, the term of this patent is extended or adjusted under 35 U.S.C. 154(b) by 308 days.

(21) Appl. No.: 11/862,302

(22) Filed: Sep. 27, 2007

(65) Prior Publication Data

US 2009/0087326 A1   Apr. 2, 2009

(51) Int. Cl.
*F04B 43/08* (2006.01)
*F04B 43/12* (2006.01)

(52) U.S. Cl. ................. 417/477.2; 417/477.11

(58) Field of Classification Search ........... 417/477.2, 417/474, 475, 476, 477.1, 477.3, 477.4, 477.5, 417/477.6, 477.7, 477.8, 477.9, 477.11, 477.12, 417/477.13, 477.14, 478
See application file for complete search history.

(56) References Cited

U.S. PATENT DOCUMENTS

| | | | |
|---|---|---|---|
| 3,011,684 A * | 12/1961 | Corneil ................. | 222/214 |
| 3,353,491 A * | 11/1967 | Bastian ................. | 417/477.9 |
| 3,921,622 A | 11/1975 | Cole | |
| 3,927,955 A * | 12/1975 | Spinosa et al. ........ | 417/477.3 |
| 3,963,023 A | 6/1976 | Hankinson | |
| 4,138,205 A * | 2/1979 | Wallach ................ | 417/360 |
| 4,178,138 A | 12/1979 | Iles | |
| 4,187,057 A | 2/1980 | Xanthopoulos | |
| 4,189,286 A * | 2/1980 | Murry et al. ........... | 417/477.11 |
| 4,210,138 A * | 7/1980 | Jess et al. ............ | 604/67 |
| 4,256,437 A | 3/1981 | Brown | |
| 4,418,565 A | 12/1983 | St. John | |
| 4,460,358 A | 7/1984 | Somerville et al. | |
| 4,519,754 A * | 5/1985 | Minick .................. | 417/477.11 |
| 4,537,561 A | 8/1985 | Xanthopoulos | |
| 4,565,500 A | 1/1986 | Jeensalute et al. | |
| 4,599,055 A | 7/1986 | Dykstra | |
| 4,673,334 A | 6/1987 | Allington et al. | |
| 4,722,224 A | 2/1988 | Scheller et al. | |
| 4,735,558 A | 4/1988 | Kienholz et al. | |
| 4,764,116 A | 8/1988 | Shoher et al. | |
| 4,764,166 A | 8/1988 | Spani | |
| 4,798,580 A | 1/1989 | DeMeo et al. | |
| 4,821,558 A | 4/1989 | Pastrone et al. | |
| 4,846,792 A | 7/1989 | Bobo, Jr. et al. | |

(Continued)

FOREIGN PATENT DOCUMENTS

CA   2479707   3/2005

(Continued)

OTHER PUBLICATIONS

Machine Translation of EP1393762A1.*

(Continued)

*Primary Examiner* — Devon C Kramer
*Assistant Examiner* — Nathan Zollinger
(74) *Attorney, Agent, or Firm* — Hodgson Russ LLP

(57) ABSTRACT

A peristaltic pump assembly includes a pump body including a mounting pin coupled thereto. A removable cassette is slidably received on the mounting pin and is secured to the pump body via a retaining feature. The mounting pin is also configured to allow the removable cassette to rotate into and/or out of an installed position, or to position(s) therebetween.

11 Claims, 3 Drawing Sheets

U.S. PATENT DOCUMENTS

| | | |
|---|---|---|
| 4,856,972 A * | 8/1989 | Van Benschoten et al. ............... 417/477.11 |
| 4,863,425 A | 9/1989 | Slate et al. |
| 4,865,584 A | 9/1989 | Epstein et al. |
| 4,884,013 A | 11/1989 | Jackson et al. |
| 4,886,431 A | 12/1989 | Soderquist et al. |
| 4,909,713 A | 3/1990 | Finsterwald et al. |
| 4,943,279 A | 7/1990 | Samiotes et al. |
| 4,944,191 A | 7/1990 | Pastrone et al. |
| 4,950,235 A | 8/1990 | Slate et al. |
| 4,950,245 A | 8/1990 | Brown et al. |
| 4,978,335 A | 12/1990 | Arthur, III |
| 4,979,940 A | 12/1990 | Bobo, Jr. et al. |
| 4,981,467 A | 1/1991 | Bobo, Jr. et al. |
| 5,000,663 A | 3/1991 | Gorton |
| 5,006,110 A | 4/1991 | Garrison et al. |
| 5,011,378 A | 4/1991 | Brown et al. |
| 5,041,086 A | 8/1991 | Koenig et al. |
| 5,053,747 A | 10/1991 | Slate et al. |
| 5,059,171 A | 10/1991 | Bridge et al. |
| 5,064,412 A | 11/1991 | Henke et al. |
| 5,078,683 A | 1/1992 | Sancoff et al. |
| 5,096,385 A | 3/1992 | Georgi et al. |
| 5,098,380 A | 3/1992 | Aizawa et al. |
| 5,102,392 A | 4/1992 | Sakai et al. |
| 5,106,366 A | 4/1992 | Steppe |
| 5,116,203 A | 5/1992 | Natwick et al. |
| 5,125,891 A | 6/1992 | Hossain et al. |
| 5,126,616 A | 6/1992 | Gorton et al. |
| 5,163,900 A | 11/1992 | Wortrich |
| 5,176,631 A | 1/1993 | Koenig |
| 5,177,993 A | 1/1993 | Beckman et al. |
| 5,181,910 A | 1/1993 | Scanlon |
| 5,191,795 A | 3/1993 | Fellingham et al. |
| 5,195,960 A | 3/1993 | Hossain et al. |
| 5,213,483 A | 5/1993 | Flaherty et al. |
| 5,219,330 A | 6/1993 | Bollish et al. |
| 5,242,408 A | 9/1993 | Jhuboo et al. |
| 5,256,156 A | 10/1993 | Kern et al. |
| 5,256,157 A | 10/1993 | Samiotes et al. |
| 5,267,956 A | 12/1993 | Beuchat |
| 5,282,787 A | 2/1994 | Wortrich |
| 5,292,306 A | 3/1994 | Wynkoop et al. |
| 5,317,506 A | 5/1994 | Coutre et al. |
| 5,328,460 A | 7/1994 | Lord et al. |
| 5,337,747 A | 8/1994 | Neftel |
| 5,338,157 A | 8/1994 | Blomquist |
| 5,356,378 A | 10/1994 | Doan |
| 5,380,173 A | 1/1995 | Hellstrom |
| 5,387,088 A | 2/1995 | Knapp et al. |
| 5,394,732 A | 3/1995 | Johnson et al. |
| 5,395,320 A | 3/1995 | Padda et al. |
| 5,397,222 A | 3/1995 | Moss et al. |
| 5,427,509 A | 6/1995 | Chapman et al. |
| 5,429,602 A | 7/1995 | Hauser |
| 5,433,588 A | 7/1995 | Monk et al. |
| 5,445,506 A | 8/1995 | Afflerbaugh et al. |
| 5,447,417 A | 9/1995 | Kuhl et al. |
| 5,462,416 A | 10/1995 | Dennehey et al. |
| 5,480,294 A | 1/1996 | Di Perna et al. |
| 5,480,386 A | 1/1996 | Brohy et al. |
| 5,482,438 A | 1/1996 | Anderson et al. |
| 5,482,446 A | 1/1996 | Williamson et al. |
| 5,485,408 A | 1/1996 | Blomquist |
| 5,501,665 A | 3/1996 | Jhuboo et al. |
| 5,514,102 A | 5/1996 | Winterer et al. |
| 5,515,713 A | 5/1996 | Saugues et al. |
| 5,518,378 A | 5/1996 | Neftel et al. |
| 5,537,853 A | 7/1996 | Finburgh et al. |
| 5,538,405 A | 7/1996 | Patno et al. |
| D376,848 S | 12/1996 | Zeilig et al. |
| 5,588,815 A | 12/1996 | Zaleski, II |
| 5,601,420 A | 2/1997 | Warner et al. |
| 5,609,575 A | 3/1997 | Larson et al. |
| 5,620,312 A | 4/1997 | Hyman et al. |
| 5,626,563 A | 5/1997 | Dodge et al. |
| 5,628,619 A | 5/1997 | Wilson |
| D380,260 S | 6/1997 | Hyman |
| 5,637,093 A | 6/1997 | Hyman et al. |
| 5,646,727 A | 7/1997 | Hammer et al. |
| 5,647,853 A | 7/1997 | Feldmann et al. |
| 5,655,897 A | 8/1997 | Neftel et al. |
| 5,657,000 A | 8/1997 | Ellingboe |
| 5,658,250 A | 8/1997 | Blomquist et al. |
| 5,669,877 A | 9/1997 | Blomquist |
| 5,676,530 A | 10/1997 | Nazarifar |
| 5,680,111 A | 10/1997 | Danby et al. |
| 5,681,285 A | 10/1997 | Ford et al. |
| 5,683,367 A | 11/1997 | Jordan et al. |
| 5,685,844 A | 11/1997 | Marttila |
| 5,695,473 A | 12/1997 | Olsen |
| 5,709,539 A | 1/1998 | Hammer et al. |
| 5,713,856 A | 2/1998 | Eggers et al. |
| 5,718,568 A | 2/1998 | Neftel et al. |
| 5,720,721 A | 2/1998 | Dumas et al. |
| 5,741,125 A | 4/1998 | Neftel et al. |
| 5,752,813 A * | 5/1998 | Tyner et al. ............... 417/477.2 |
| 5,755,691 A | 5/1998 | Hilborne |
| 5,759,015 A | 6/1998 | Van Lintel et al. |
| 5,764,159 A | 6/1998 | Neftel |
| 5,766,155 A | 6/1998 | Hyman et al. |
| 5,772,635 A | 6/1998 | Dastur et al. |
| 5,782,611 A | 7/1998 | Neftel et al. |
| 5,782,805 A | 7/1998 | Meinzer et al. |
| 5,788,669 A | 8/1998 | Peterson |
| 5,791,880 A | 8/1998 | Wilson |
| 5,795,317 A | 8/1998 | Brierton et al. |
| 5,795,327 A | 8/1998 | Wilson et al. |
| 5,800,387 A | 9/1998 | Duffy et al. |
| 5,811,659 A | 9/1998 | Giebler |
| 5,827,223 A | 10/1998 | Butterfield |
| 5,827,262 A | 10/1998 | Neftel et al. |
| 5,836,910 A | 11/1998 | Duffy et al. |
| 5,840,068 A | 11/1998 | Cartledge et al. |
| 5,842,841 A | 12/1998 | Danby et al. |
| 5,843,035 A | 12/1998 | Bowman et al. |
| 5,848,988 A | 12/1998 | Davis |
| 5,853,386 A | 12/1998 | Davis et al. |
| 5,897,524 A | 4/1999 | Wortrich et al. |
| 5,904,668 A | 5/1999 | Hyman et al. |
| 5,906,589 A | 5/1999 | Gordon et al. |
| 5,927,956 A | 7/1999 | Lim et al. |
| 5,928,196 A | 7/1999 | Johnson et al. |
| 5,935,099 A | 8/1999 | Peterson et al. |
| 5,935,106 A | 8/1999 | Olsen |
| 5,938,413 A | 8/1999 | Makino et al. |
| 5,941,846 A | 8/1999 | Duffy et al. |
| 5,954,485 A | 9/1999 | Johnson et al. |
| 5,961,487 A | 10/1999 | Davis |
| 5,968,014 A | 10/1999 | Neftel et al. |
| 5,984,894 A | 11/1999 | Poulsen et al. |
| 5,989,222 A | 11/1999 | Cole et al. |
| 5,993,420 A | 11/1999 | Hyman et al. |
| 6,013,057 A | 1/2000 | Danby et al. |
| 6,059,765 A | 5/2000 | Cole et al. |
| 6,068,612 A | 5/2000 | Bowman et al. |
| 6,077,055 A | 6/2000 | Vilks |
| 6,077,246 A | 6/2000 | Kullas et al. |
| 6,085,574 A | 7/2000 | Neftel et al. |
| 6,106,498 A | 8/2000 | Friedli et al. |
| 6,109,895 A | 8/2000 | Ray et al. |
| 6,110,153 A | 8/2000 | Davis et al. |
| 6,120,490 A | 9/2000 | Neftel |
| 6,123,524 A | 9/2000 | Danby et al. |
| 6,129,517 A | 10/2000 | Danby et al. |
| 6,129,699 A | 10/2000 | Haight et al. |
| 6,142,008 A | 11/2000 | Cole et al. |
| 6,146,109 A | 11/2000 | Davis et al. |
| 6,195,887 B1 | 3/2001 | Danby et al. |
| 6,203,296 B1 | 3/2001 | Ray et al. |
| 6,203,528 B1 | 3/2001 | Deckert et al. |
| 6,212,936 B1 | 4/2001 | Meisberger |
| 6,213,723 B1 | 4/2001 | Danby et al. |
| 6,213,738 B1 | 4/2001 | Danby et al. |
| 6,231,320 B1 | 5/2001 | Lawless et al. |
| 6,234,992 B1 | 5/2001 | Haight et al. |

| | | |
|---|---|---|
| 6,241,704 B1 | 6/2001 | Peterson et al. |
| 6,248,067 B1 | 6/2001 | Causey, III et al. |
| 6,261,262 B1 | 7/2001 | Briggs et al. |
| 6,269,340 B1 | 7/2001 | Ford et al. |
| D446,854 S | 8/2001 | Cheney, II et al. |
| 6,270,673 B1 | 8/2001 | Belt et al. |
| 6,280,430 B1 | 8/2001 | Neftel et al. |
| 6,293,926 B1 | 9/2001 | Sorensen et al. |
| 6,328,712 B1 | 12/2001 | Cartledge et al. |
| 6,358,225 B1 | 3/2002 | Butterfield |
| 6,362,591 B1 | 3/2002 | Moberg |
| 6,364,279 B1 | 4/2002 | Neftel et al. |
| 6,423,029 B1 | 7/2002 | Elsberry |
| 6,447,481 B1 | 9/2002 | Duchon et al. |
| 6,468,059 B2 | 10/2002 | Haser et al. |
| 6,475,180 B2 | 11/2002 | Peterson et al. |
| 6,489,896 B1 | 12/2002 | Platt et al. |
| 6,519,569 B1 | 2/2003 | White et al. |
| 6,539,250 B1 | 3/2003 | Bettinger |
| 6,551,276 B1 | 4/2003 | Mann et al. |
| 6,554,791 B1 | 4/2003 | Cartledge et al. |
| 6,554,798 B1 | 4/2003 | Mann et al. |
| 6,555,986 B2 | 4/2003 | Moberg |
| 6,558,320 B1 | 5/2003 | Causey, III et al. |
| 6,558,343 B1 | 5/2003 | Neftel |
| 6,572,349 B2 | 6/2003 | Sorensen et al. |
| 6,572,604 B1 | 6/2003 | Platt et al. |
| 6,632,190 B2 | 10/2003 | Simonini et al. |
| 6,641,533 B2 | 11/2003 | Causey, III et al. |
| 6,648,861 B2 | 11/2003 | Platt et al. |
| 6,670,885 B2 | 12/2003 | Kosaka |
| 6,689,091 B2 | 2/2004 | Bui et al. |
| 6,716,193 B1 | 4/2004 | Neftel |
| 6,731,216 B2 | 5/2004 | Ho et al. |
| 6,742,992 B2 | 6/2004 | Davis |
| 6,790,198 B1 | 9/2004 | White et al. |
| 6,809,653 B1 | 10/2004 | Mann et al. |
| 6,835,049 B2 | 12/2004 | Ray |
| 6,852,104 B2 | 2/2005 | Blomquist |
| 6,872,200 B2 | 3/2005 | Mann et al. |
| 6,889,556 B2 | 5/2005 | Steger |
| 6,936,029 B2 | 8/2005 | Mann et al. |
| 6,942,637 B2 | 9/2005 | Cartledge et al. |
| 6,962,488 B2 | 11/2005 | Davis et al. |
| 6,966,895 B2 | 11/2005 | Tribe |
| 6,979,326 B2 | 12/2005 | Mann et al. |
| 6,985,870 B2 | 1/2006 | Martucci et al. |
| 6,997,905 B2 | 2/2006 | Gillespie, Jr. et al. |
| 6,997,920 B2 | 2/2006 | Mann et al. |
| 6,999,854 B2 | 2/2006 | Roth |
| 7,001,153 B2 | 2/2006 | McDowell et al. |
| 7,018,182 B2 | 3/2006 | O'Mahony et al. |
| 7,025,743 B2 | 4/2006 | Mann et al. |
| 7,048,193 B2 | 5/2006 | Tsukada et al. |
| 7,070,578 B2 | 7/2006 | Leukanech et al. |
| 7,074,205 B1 | 7/2006 | Duffy et al. |
| 7,098,803 B2 | 8/2006 | Mann et al. |
| 7,109,878 B2 | 9/2006 | Mann et al. |
| 7,117,041 B2 | 10/2006 | Engleson et al. |
| 7,141,037 B2 | 11/2006 | Butterfield et al. |
| 7,150,735 B2 | 12/2006 | Hickle |
| 7,160,284 B2 | 1/2007 | Ullestad et al. |
| 7,193,521 B2 | 3/2007 | Moberg et al. |
| 7,195,607 B2 | 3/2007 | Westberg et al. |
| 7,204,823 B2 | 4/2007 | Estes et al. |
| 7,214,038 B2 | 5/2007 | Saxer et al. |
| 7,223,079 B2 | 5/2007 | Ortega et al. |
| 7,236,936 B2 | 6/2007 | White et al. |
| 7,239,941 B2 | 7/2007 | Mori et al. |
| 7,264,148 B2 | 9/2007 | Tachibana |
| 7,311,691 B2 | 12/2007 | Cartledge et al. |
| 2001/0004444 A1 | 6/2001 | Haser et al. |
| 2001/0049608 A1 | 12/2001 | Hochman |
| 2002/0002326 A1 | 1/2002 | Causey, III et al. |
| 2002/0016570 A1 | 2/2002 | Cartledge et al. |
| 2002/0029776 A1 | 3/2002 | Blomquist |
| 2002/0077852 A1 | 6/2002 | Ford et al. |
| 2002/0077856 A1 | 6/2002 | Pawlikowski et al. |
| 2002/0099334 A1 | 7/2002 | Hanson et al. |
| 2002/0104370 A1 | 8/2002 | Steger et al. |
| 2002/0138155 A1 | 9/2002 | Bristol |
| 2002/0169636 A1 | 11/2002 | Eggers et al. |
| 2002/0183693 A1 | 12/2002 | Peterson et al. |
| 2002/0193679 A1 | 12/2002 | Malave et al. |
| 2003/0004458 A1 | 1/2003 | Platt et al. |
| 2003/0060765 A1 | 3/2003 | Campbell et al. |
| 2003/0106553 A1 | 6/2003 | Vanderveen |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141368 A1 | 7/2003 | Pascual et al. |
| 2003/0141981 A1 | 7/2003 | Bui et al. |
| 2003/0144878 A1 | 7/2003 | Wilkes et al. |
| 2003/0144881 A1 | 7/2003 | Talachian et al. |
| 2003/0144882 A1 | 7/2003 | Talachian et al. |
| 2003/0201697 A1 | 10/2003 | Richardson |
| 2003/0204414 A1 | 10/2003 | Wilkes et al. |
| 2003/0204416 A1 | 10/2003 | Radpay et al. |
| 2003/0204419 A1 | 10/2003 | Wilkes et al. |
| 2003/0204420 A1 | 10/2003 | Wilkes et al. |
| 2003/0212364 A1 | 11/2003 | Mann et al. |
| 2003/0222548 A1 | 12/2003 | Richardson et al. |
| 2004/0010425 A1 | 1/2004 | Wilkes et al. |
| 2004/0019464 A1 | 1/2004 | Martucci et al. |
| 2004/0019607 A1 | 1/2004 | Moubayed et al. |
| 2004/0057856 A1 | 3/2004 | Saxer et al. |
| 2004/0064435 A1 | 4/2004 | Moubayed et al. |
| 2004/0073095 A1 | 4/2004 | Causey, III et al. |
| 2004/0078231 A1 | 4/2004 | Wilkes et al. |
| 2004/0103897 A1 | 6/2004 | Hickle et al. |
| 2004/0107965 A1 | 6/2004 | Hickle et al. |
| 2004/0116862 A1 | 6/2004 | Ray |
| 2004/0121767 A1 | 6/2004 | Simpson et al. |
| 2004/0158193 A1 | 8/2004 | Bui et al. |
| 2004/0167465 A1 | 8/2004 | Mihai et al. |
| 2004/0167495 A1 | 8/2004 | Neftel |
| 2004/0167804 A1 | 8/2004 | Simpson et al. |
| 2004/0172222 A1 | 9/2004 | Simpson et al. |
| 2004/0172300 A1 | 9/2004 | Mihai et al. |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0176984 A1 | 9/2004 | White et al. |
| 2004/0193325 A1 | 9/2004 | Bonderud et al. |
| 2004/0225252 A1 | 11/2004 | Gillespie, Jr. et al. |
| 2005/0020978 A1 | 1/2005 | Vollenweider |
| 2005/0021006 A1 | 1/2005 | Tonnies |
| 2005/0021368 A1 | 1/2005 | Burkeen et al. |
| 2005/0022274 A1 | 1/2005 | Campbell et al. |
| 2005/0029277 A1 | 2/2005 | Tachibana |
| 2005/0055242 A1 | 3/2005 | Bello et al. |
| 2005/0055244 A1 | 3/2005 | Mullan et al. |
| 2005/0065817 A1 | 3/2005 | Mihai et al. |
| 2005/0069437 A1 | 3/2005 | Mittelstein et al. |
| 2005/0089994 A1 | 4/2005 | Neftel |
| 2005/0095152 A1 | 5/2005 | Dale |
| 2005/0096593 A1 | 5/2005 | Pope et al. |
| 2005/0101907 A1 | 5/2005 | Sondeen et al. |
| 2005/0118048 A1 | 6/2005 | Traxinger |
| 2005/0124929 A1 | 6/2005 | Katz et al. |
| 2005/0137530 A1 | 6/2005 | Campbell et al. |
| 2005/0137653 A1 | 6/2005 | Friedman et al. |
| 2005/0139651 A1 | 6/2005 | Lim et al. |
| 2005/0143864 A1 | 6/2005 | Blomquist |
| 2005/0148869 A1 | 7/2005 | Masuda |
| 2005/0154368 A1 | 7/2005 | Lim et al. |
| 2005/0171513 A1 | 8/2005 | Mann et al. |
| 2005/0177395 A1 | 8/2005 | Blomquist |
| 2005/0182366 A1 | 8/2005 | Vogt et al. |
| 2005/0196307 A1 | 9/2005 | Limoges |
| 2005/0214129 A1 | 9/2005 | Greene et al. |
| 2005/0234382 A1 | 10/2005 | Tonelli et al. |
| 2005/0277873 A1 | 12/2005 | Stewart et al. |
| 2005/0277890 A1 | 12/2005 | Stewart et al. |
| 2005/0277911 A1 | 12/2005 | Stewart et al. |
| 2005/0278073 A1 | 12/2005 | Roth |
| 2005/0283210 A1 | 12/2005 | Blischak et al. |
| 2006/0001550 A1 | 1/2006 | Mann et al. |

| | | | | | | |
|---|---|---|---|---|---|---|
| 2006/0002799 A1 | 1/2006 | Schann et al. | | EP | 0 293 081 A1 | 11/1988 |
| 2006/0002805 A1 | 1/2006 | Schann et al. | | EP | 0 293 591 A2 | 12/1988 |
| 2006/0007017 A1 | 1/2006 | Mann et al. | | EP | 0 036 130 A1 | 3/1989 |
| 2006/0009734 A1 | 1/2006 | Martin | | EP | 0 319 275 A1 | 6/1989 |
| 2006/0027523 A1 | 2/2006 | Van Lintel et al. | | EP | 0 327 209 A2 | 8/1989 |
| 2006/0058804 A1 | 3/2006 | Mollstam | | EP | 0 332 330 | 9/1989 |
| 2006/0100746 A1 | 5/2006 | Leibner-Druska | | EP | 0 335 385 A2 | 10/1989 |
| 2006/0106649 A1 | 5/2006 | Eggers et al. | | EP | 0 362 822 A2 | 4/1990 |
| 2006/0116639 A1 | 6/2006 | Russell | | EP | 0 364 010 A2 | 4/1990 |
| 2006/0122867 A1 | 6/2006 | Eggers et al. | | EP | 362822 | 4/1990 |
| 2006/0129429 A1 | 6/2006 | Moubayed et al. | | EP | 0 396 003 A2 | 11/1990 |
| 2006/0132283 A1 | 6/2006 | Eberhart et al. | | EP | 399119 | 11/1990 |
| 2006/0136271 A1 | 6/2006 | Eggers et al. | | EP | 0 416 910 | 3/1991 |
| 2006/0143051 A1 | 6/2006 | Eggers et al. | | EP | 0 416 911 | 3/1991 |
| 2006/0177328 A1* | 8/2006 | Nordell et al. ............ 417/477.2 | | EP | 0 416 912 | 3/1991 |
| 2006/0184121 A1 | 8/2006 | Brockman et al. | | EP | 0 419 094 | 3/1991 |
| 2006/0184123 A1 | 8/2006 | Gillespie, Jr. et al. | | EP | 0 431 310 | 6/1991 |
| 2006/0184154 A1 | 8/2006 | Moberg et al. | | EP | 0 446 605 | 9/1991 |
| 2006/0189923 A1 | 8/2006 | Neftel et al. | | EP | 0 453 211 | 10/1991 |
| 2006/0190302 A1 | 8/2006 | Eggers et al. | | EP | 0 468 603 | 1/1992 |
| 2006/0200369 A1 | 9/2006 | Batch et al. | | EP | 0 495 538 A2 | 7/1992 |
| 2006/0202859 A1 | 9/2006 | Mastrototaro et al. | | EP | 0 496 436 A2 | 7/1992 |
| 2006/0219644 A1 | 10/2006 | O'Hara, Jr. et al. | | EP | 0 497 041 | 8/1992 |
| 2006/0229551 A1 | 10/2006 | Martinez | | EP | 0 499 903 | 8/1992 |
| 2006/0243804 A1 | 11/2006 | Christoffersen et al. | | EP | 0 503 670 | 9/1992 |
| 2006/0258985 A1 | 11/2006 | Russell | | EP | 0 508 556 A1 | 10/1992 |
| 2006/0271020 A1 | 11/2006 | Huang et al. | | EP | 0 524 605 | 1/1993 |
| 2006/0287884 A1 | 12/2006 | Sandy et al. | | EP | 0 544 393 | 6/1993 |
| 2006/0287887 A1 | 12/2006 | Hutchinson et al. | | EP | 0 554 716 | 8/1993 |
| 2007/0048161 A1 | 3/2007 | Moubayed | | EP | 690961 | 1/1995 |
| 2007/0058412 A1 | 3/2007 | Wang et al. | | EP | 0 648 509 | 4/1995 |
| 2007/0060871 A1 | 3/2007 | Istoc et al. | | EP | 0646382 | 4/1995 |
| 2007/0073228 A1 | 3/2007 | Mernoe et al. | | EP | 0646383 | 4/1995 |
| 2007/0073235 A1 | 3/2007 | Estes et al. | | EP | 0 681 847 | 11/1995 |
| 2007/0073236 A1 | 3/2007 | Mernoe et al. | | EP | 0 731 275 | 9/1996 |
| 2007/0077152 A1 | 4/2007 | Knauper et al. | | EP | 0 891 784 | 1/1999 |
| 2007/0078370 A1 | 4/2007 | Shener et al. | | EP | 0 893 131 | 1/1999 |
| 2007/0078431 A1 | 4/2007 | Hudson et al. | | EP | 0 893 132 | 1/1999 |
| 2007/0083153 A1 | 4/2007 | Haar | | EP | 0 898 981 | 3/1999 |
| 2007/0083292 A1 | 4/2007 | Knauper et al. | | EP | 0 899 564 | 3/1999 |
| 2007/0088249 A1 | 4/2007 | Duffy et al. | | EP | 0 919 250 | 6/1999 |
| 2007/0088269 A1 | 4/2007 | Valego et al. | | EP | 0 931 555 | 7/1999 |
| 2007/0100316 A1 | 5/2007 | Traxinger | | EP | 0 934 752 | 8/1999 |
| 2007/0104599 A1 | 5/2007 | Michels et al. | | EP | 0 985 420 | 3/2000 |
| 2007/0106218 A1 | 5/2007 | Yodfat et al. | | EP | 0 985 421 | 3/2000 |
| 2007/0107490 A1 | 5/2007 | Artsyukhovich et al. | | EP | 0 988 867 | 3/2000 |
| 2007/0118405 A1 | 5/2007 | Campbell et al. | | EP | 1 045 146 | 10/2000 |
| 2007/0148010 A1 | 6/2007 | Michels et al. | | EP | 1 101 503 | 5/2001 |
| 2007/0156033 A1 | 7/2007 | Causey, III et al. | | EP | 1 101 504 | 5/2001 |
| 2007/0156092 A1 | 7/2007 | Estes et al. | | EP | 1108891 | 6/2001 |
| 2007/0167905 A1 | 7/2007 | Estes et al. | | EP | 1225445 | 7/2002 |
| 2007/0167912 A1 | 7/2007 | Causey et al. | | EP | 1 251 276 | 10/2002 |
| 2007/0173762 A1 | 7/2007 | Estes et al. | | EP | 1 357 372 | 10/2003 |
| 2007/0179444 A1 | 8/2007 | Causey et al. | | EP | 1 391 215 | 2/2004 |
| 2007/0212240 A1 | 9/2007 | Voyeux et al. | | EP | 1 400 691 | 3/2004 |
| 2007/0217932 A1 | 9/2007 | Voyeux et al. | | EP | 1393762 | 3/2004 |
| 2008/0015507 A1 | 1/2008 | Cartledge et al. | | EP | 1393762 A1 * | 3/2004 |
| 2008/0045902 A1 | 2/2008 | Estes et al. | | EP | 1 501 037 | 1/2005 |
| 2008/0045903 A1 | 2/2008 | Estes et al. | | EP | 1 532 995 | 5/2005 |
| 2008/0045904 A1 | 2/2008 | Estes et al. | | EP | 1 535 637 | 6/2005 |
| 2008/0045931 A1 | 2/2008 | Estes et al. | | EP | 1 537 886 | 6/2005 |
| | | | | EP | 1 563 859 | 8/2005 |
| FOREIGN PATENT DOCUMENTS | | | | EP | 1576971 | 9/2005 |
| DE | 41 04814 | 3/1991 | | EP | 1 609 500 | 12/2005 |
| DE | 4037797 | 2/1992 | | EP | 1 612 423 | 1/2006 |
| DE | 4307758 | 9/1994 | | EP | 1612424 | 1/2006 |
| DE | 19525926 | 11/1996 | | EP | 1616588 | 1/2006 |
| DE | 29806966 U1 | 9/1998 | | EP | 1 642 608 | 4/2006 |
| DE | 19738146 | 3/1999 | | EP | 1 739 585 | 1/2007 |
| DE | 20000965 U1 | 4/2000 | | EP | 1 762 263 | 3/2007 |
| DE | 199 16 876 | 11/2000 | | EP | 1 769 812 | 4/2007 |
| DE | 10020496 | 11/2000 | | EP | 1 769 813 | 4/2007 |
| DE | 199 60 668 | 8/2001 | | EP | 1 769 815 | 4/2007 |
| DE | 10022022 | 11/2001 | | EP | 1772162 | 4/2007 |
| DE | 201 01 082 | 7/2002 | | ES | 2238897 | 9/2005 |
| DE | 202 06 474 | 10/2003 | | FR | 2 690 622 | 11/1993 |
| DE | 102 44 090 | 4/2004 | | FR | 2792840 | 11/2000 |
| DE | 10359735 | 7/2005 | | GB | 1578022 | 10/1980 |
| EP | 164020 | 12/1985 | | GB | 2109474 | 6/1983 |

| | | |
|---|---|---|
| GB | 2285837 A | 7/1995 |
| GB | 2309801 A | 8/1997 |
| GB | 2 312 022 | 10/1997 |
| GB | 2 312 046 | 10/1997 |
| GB | 2 312 055 | 10/1997 |
| GB | 2 338 752 | 12/1999 |
| GB | 2 338 753 | 12/1999 |
| GB | 2 338 754 | 12/1999 |
| GB | 2 338 755 | 12/1999 |
| GB | 2 338 756 | 12/1999 |
| GB | 2 338 757 | 12/1999 |
| GB | 2 338 758 | 12/1999 |
| GB | 2 338 759 | 12/1999 |
| GB | 2 338 760 | 12/1999 |
| GB | 2 338 992 | 12/1999 |
| GB | 2 342 188 | 4/2000 |
| GB | 2 342 189 | 4/2000 |
| GB | 2 417 052 | 2/2006 |
| JP | 9220279 | 8/1997 |
| JP | 07308379 | 4/1998 |
| JP | 2001218841 | 8/2001 |
| JP | 06205829 | 11/2001 |
| JP | 2004000498 | 1/2004 |
| JP | 2004162647 | 6/2004 |
| JP | 2005095577 | 4/2005 |
| JP | 2006034719 | 2/2006 |
| JP | 3124022 | 7/2006 |
| KR | 10-0516727 | 9/2005 |
| KR | 10-0553384 | 2/2006 |
| KR | 10-0561243 | 3/2006 |
| KR | 10-0607128 | 7/2006 |
| KR | 10-0755528 | 8/2007 |
| WO | WO 91/00113 | 1/1991 |
| WO | WO 91/04759 | 4/1991 |
| WO | WO 91/12848 | 9/1991 |
| WO | WO 92/15349 | 9/1992 |
| WO | WO 92/18175 | 10/1992 |
| WO | WO 93/21978 | 11/1993 |
| WO | WO 93/24893 | 12/1993 |
| WO | WO 93/25816 | 12/1993 |
| WO | WO 94/08647 | 4/1994 |
| WO | WO 95/06817 | 3/1995 |
| WO | WO 9517600 | 5/1995 |
| WO | WO 95/17913 | 7/1995 |
| WO | WO 95/24229 | 9/1995 |
| WO | WO 96/01371 | 1/1996 |
| WO | WO 96/03168 | 2/1996 |
| WO | WO 96/08278 | 3/1996 |
| WO | WO 96/08717 | 3/1996 |
| WO | WO 96/20745 | 7/1996 |
| WO | WO 96/20746 | 7/1996 |
| WO | WO 96/27402 | 9/1996 |
| WO | WO 96/28209 | 9/1996 |
| WO | WO 96/34648 | 11/1996 |
| WO | WO 96/36389 | 11/1996 |
| WO | WO 97/02059 | 1/1997 |
| WO | WO 97/07843 | 3/1997 |
| WO | WO 97/21456 | 6/1997 |
| WO | WO 97/32129 | 9/1997 |
| WO | WO 97/37703 | 10/1997 |
| WO | WO 97/37704 | 10/1997 |
| WO | WO 97/37706 | 10/1997 |
| WO | WO 98/13080 | 4/1998 |
| WO | WO 98/14234 | 4/1998 |
| WO | WO 98/20918 | 5/1998 |
| WO | WO 98/56450 | 12/1998 |
| WO | WO 98/56451 | 12/1998 |
| WO | WO 98/56453 | 12/1998 |
| WO | WO 99/10029 | 3/1999 |
| WO | WO 99/22783 | 5/1999 |
| WO | WO 99/47812 | 9/1999 |
| WO | WO 99/64091 | 12/1999 |
| WO | WO 99/64093 | 12/1999 |
| WO | WO00/10628 | 3/2000 |
| WO | WO 00/16823 | 3/2000 |
| WO | WO 00/18449 | 4/2000 |
| WO | WO 00/21587 | 4/2000 |
| WO | WO 00/48112 | 8/2000 |
| WO | WO 00/51671 | 9/2000 |
| WO | WO 00/57941 | 10/2000 |
| WO | WO 00/66203 | 11/2000 |
| WO | WO 00/72181 | 11/2000 |
| WO | WO 01/23277 | 4/2001 |
| WO | WO 01/34222 | 5/2001 |
| WO | WO 01/39816 | 6/2001 |
| WO | WO 01/54566 | 8/2001 |
| WO | WO 01/97113 | 12/2001 |
| WO | WO 02/11049 | 2/2002 |
| WO | WO 02/36044 | 5/2002 |
| WO | WO 02/38204 | 5/2002 |
| WO | WO 02-43573 | 6/2002 |
| WO | WO 02/49259 | 6/2002 |
| WO | WO 02-055137 | 7/2002 |
| WO | WO 02/061281 | 8/2002 |
| WO | WO 02/066101 | 8/2002 |
| WO | WO 02/069099 | 9/2002 |
| WO | WO 02-081919 | 10/2002 |
| WO | WO03/011377 | 2/2003 |
| WO | WO03/024385 | 3/2003 |
| WO | WO 03/053503 | 7/2003 |
| WO | WO 2004/024053 | 3/2004 |
| WO | WO 2004/024214 | 3/2004 |
| WO | WO 2004/047641 | 6/2004 |
| WO | WO 2004/087241 | 10/2004 |
| WO | WO 2004/093648 | 11/2004 |
| WO | WO 2004/095379 | 11/2004 |
| WO | WO 2005/050497 | 6/2005 |
| WO | WO 2005/062751 | 7/2005 |
| WO | WO 2005/089263 | 9/2005 |
| WO | WO 2005/106251 | 11/2005 |
| WO | WO 2006/008364 | 1/2006 |
| WO | WO 2006/008376 | 1/2006 |
| WO | WO 2006/014200 | 2/2006 |
| WO | WO 2006/016122 | 2/2006 |
| WO | WO 2006/029237 | 3/2006 |
| WO | WO 2006/046242 | 5/2006 |
| WO | WO 2006/084464 | 8/2006 |
| WO | WO 2006/086701 | 8/2006 |
| WO | WO 2006/086723 | 8/2006 |
| WO | WO 2006/086735 | 8/2006 |
| WO | WO 2006/103711 | 10/2006 |
| WO | WO 2006/103712 | 10/2006 |
| WO | WO 2006/124202 | 11/2006 |
| WO | WO 2006/127905 | 11/2006 |
| WO | WO 2007/023329 | 3/2007 |
| WO | WO 2007/025268 | 3/2007 |
| WO | WO 2007/033010 | 3/2007 |
| WO | WO 2007/038059 | 4/2007 |
| WO | WO 2007/038060 | 4/2007 |
| WO | WO 2007/038091 | 4/2007 |
| WO | WO 2007/041843 | 4/2007 |
| WO | WO 2007/052277 | 5/2007 |
| WO | WO 2007/061368 | 5/2007 |
| WO | WO2008/082091 | 7/2008 |

OTHER PUBLICATIONS

U.S. Appl. No. 11/862,326, filed Sep. 27, 2007, Voltenburg et al.
U.S. Appl. No. 11/862,360, filed Sep. 27, 2007, Voltenburg et al.
International Search Report dated Dec. 1, 2008.
The International Bureau of WIPO, International Preliminary Report on Patentability in International Application No. PCT/US2008/011145, issued Mar. 30, 2010.

* cited by examiner

PERISTALTIC PUMP ASSEMBLY WITH CASSETTE AND MOUNTING PIN ARRANGEMENT

BACKGROUND

The present disclosure relates generally to peristaltic pump assemblies.

Rotary-style peristaltic pumps often generally include a cassette mounted to and supported by a pump body. In some instances, the pump body includes a cavity formed therein and configured to receive a planetary assembly of rollers. The rollers revolve together when rotationally driven by a drive shaft when the drive shaft is powered by a pump motor.

The cassette generally includes a body having a flexible tube disposed therethrough. When the cassette is mounted to the pump body, the flexible tube surrounds a portion of the assembly of rollers. In response to rotational movement of the rollers, portions of the flexible tube in contact with the rollers compress or otherwise occlude against a wall of the cassette. As a result, fluid traveling through the tube is temporarily trapped in the tube between the occluded points. The trapped fluid is released from the tube when the occlusion force on the tube is released. In this manner, fluid is urged through the tube via peristaltic wave action.

Peristaltic infusion pumps are often used to deliver fluid in a controlled manner, such as, for example, the intravenous delivery of pharmaceutical compositions to a patient. These peristaltic pumps typically use disposable cassettes, where the pump assembly is designed to accommodate the loading of the cassette, as well as the removal of the cassette from the assembly. Such designs, however, may undesirably involve relatively difficult cassette loading and removal schemes.

SUMMARY

A peristaltic pump assembly includes a pump body having a mounting pin coupled thereto. A removable cassette is slidably received on the mounting pin and is secured to the pump body via a retaining feature. The mounting pin is configured to allow the removable cassette to rotate into an installed position, out of an installed position, or to positions therebetween.

BRIEF DESCRIPTION OF THE DRAWINGS

Features and advantages of embodiment(s) of the present disclosure will become apparent by reference to the following detailed description and drawings, in which like reference numerals correspond to similar, though perhaps not identical components. Reference numerals having a previously described function may or may not be described in connection with other drawings in which they appear.

DETAILED DESCRIPTION

Embodiment(s) of the peristaltic pump assembly as disclosed herein advantageously provide a simplified pump assembly design to facilitate loading and removal of a cassette to and from a pump body. The mounting and removal processes are relatively simple and efficient, thereby eliminating the need for extensive operator training therefor. The pump assembly enabling the cassette mounting process reduces or substantially eliminates errors with respect to improper positioning of the cassette when assembled with the pump body. Audible and/or tactile feedback may also be available to ensure that the cassette is mounted properly with the pump body. The components of the pump assembly (e.g., the mounting pin) are substantially robust in design to generally withstand long-term wear and use. The pump assembly also advantageously does not require the use of a door, which has a tendency to wear down and/or break from continuous use thereof.

Figure 1:
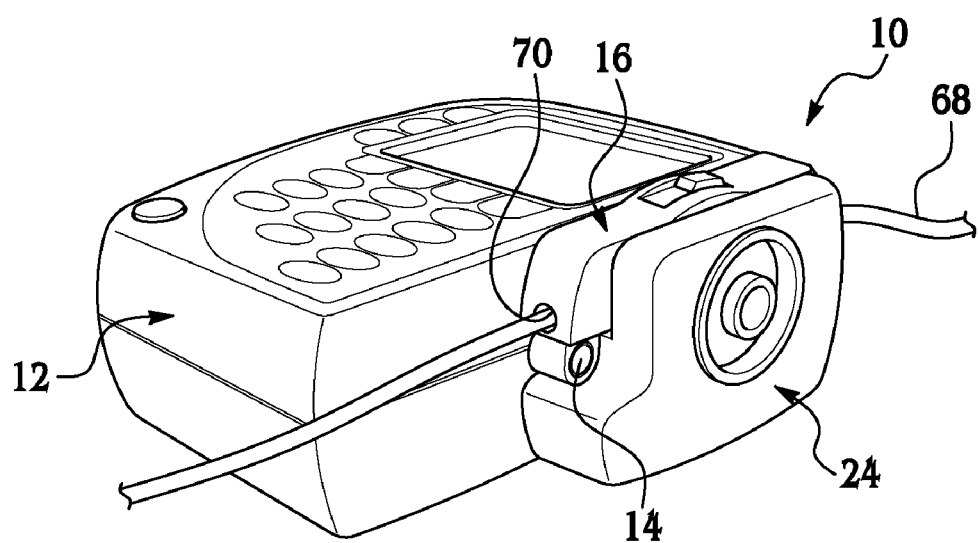
FIG. 1 is a perspective view of an example of a peristaltic pump assembly including an example of a cassette in an installed position.

With reference now to the drawings, FIG. 1 provides a peristaltic pump assembly 10 including a disposable cassette 16 in an installed position. The peristaltic pump assembly 10 includes a pump body 12 with a mounting pin 14 coupled thereto. The cassette 16 is slidably received on the mounting pin 14 and secured to the pump body 12 via a cassette retaining feature 18 (shown in FIGS. 3 and 4). The mounting pin 14 is configured to allow the cassette 16 to rotate into and/or out of the installed position, or to positions therebetween.

Figure 2:
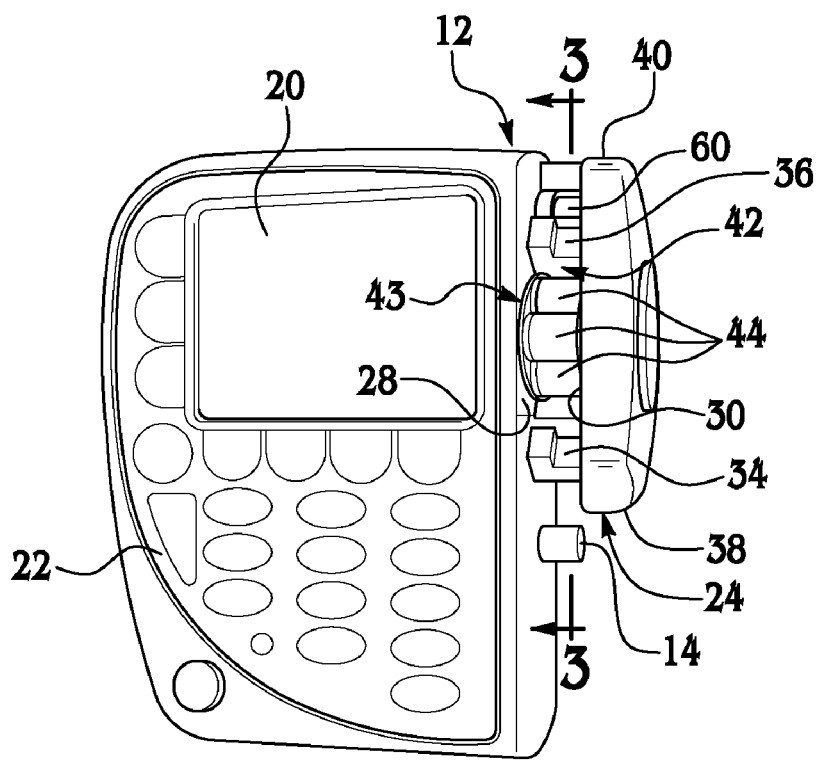
FIG. 2 is a top, perspective view of an example of a pump body for the peristaltic pump assembly of FIG. 1.

As shown in FIG. 2, the pump body 12 includes a display 20 that corresponds with a keypad 22 for inputting user information such as, for example, patient identification number, drug identification number, operator identification number, or the like. The display 20 also provides visual feedback to the operator or user of the pump 10 regarding, for example, the amount of medication administered to the patient, the flow rate of the medication, and the time for medication administration.

The pump body 12 also includes a cassette receiving portion 24 formed adjacent to the display 20. The cassette receiving portion 24 includes a partial cavity 42 defined by a floor (not shown) and two opposing walls 28, 30.

Figure 3:
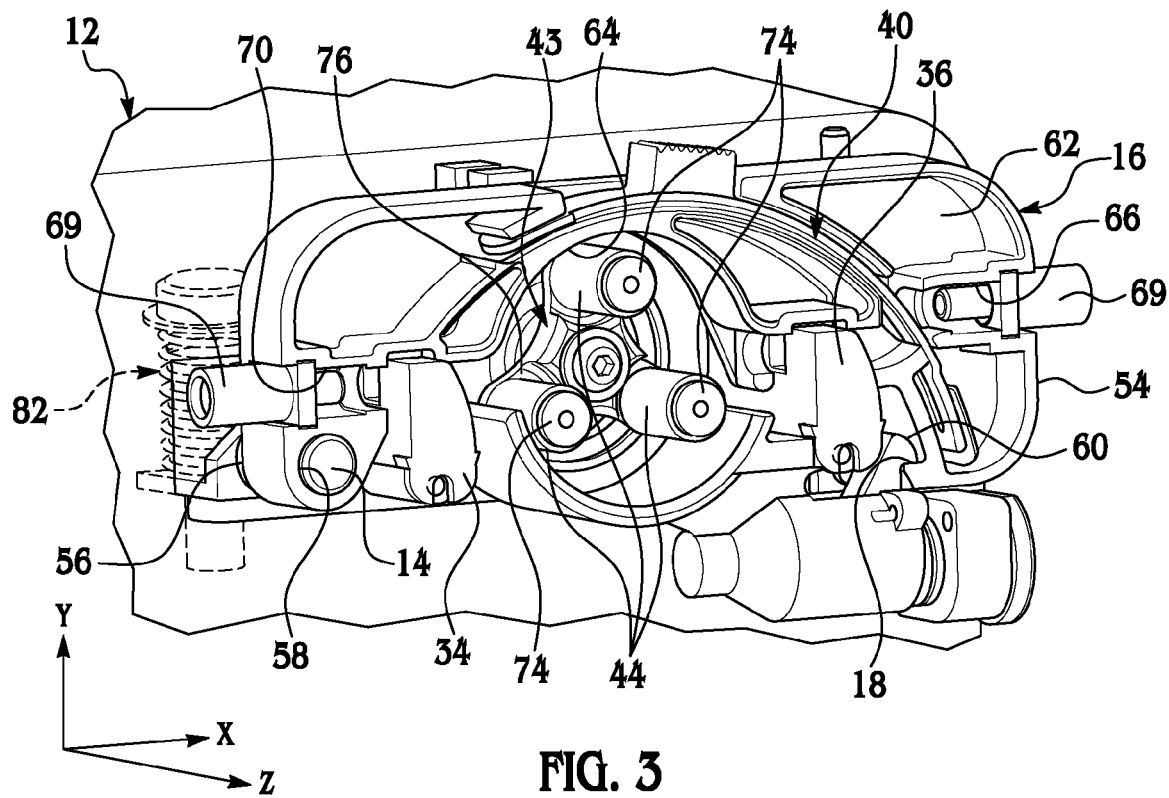
FIG. 3 is a cut-away, perspective view of the peristaltic pump assembly of FIG. 1, showing a pump body retaining feature in a closed position.
Figure 4:
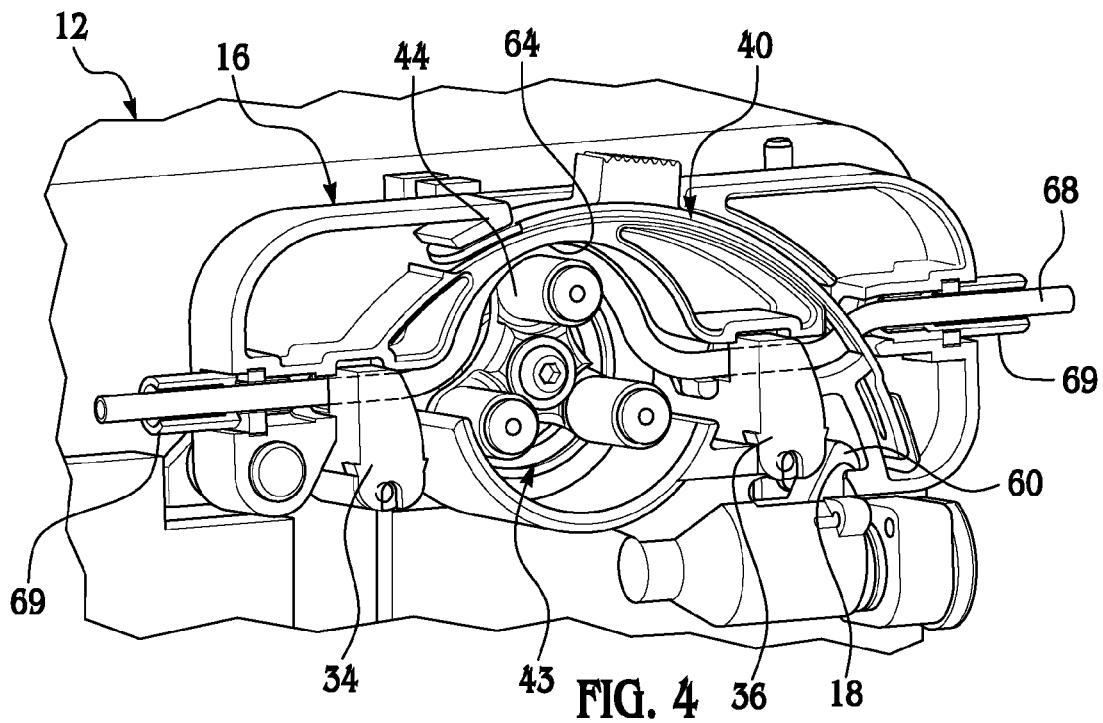
FIG. 4 is a cut-away, perspective view of the peristaltic pump assembly of FIG. 3, including a flexible tubing disposed in the cassette and pump assembly.

As shown in FIGS. 3 and 4, in an embodiment, a pressure sensor 36 is located upstream (e.g., near inlet end portion 40, shown in FIG. 2) in the cavity 42 of the cassette receiving portion 24. A second pressure sensor and/or an air-in-line sensor 34 is located downstream (e.g., near outlet end portion 38) in the cavity 42. It is to be understood that the pressure sensor(s) 36 may be any suitable pressure sensors, e.g., piezoelectric pressure sensors; and that the air-in-line sensors 34 may be any suitable sensors, e.g., ultrasonic air-in-line sensors. The pressure/air-in-line sensors 36, 34 are also generally shaped to complement the shape of the cassette 16. Further, the sensors 34, 36 in combination with the opposed walls 28, 30 are also generally configured to guide the cassette 16 and tubing 68 (as shown in FIG. 1) as the cassette 16 is placed or otherwise rotated into the installed position.

A roller mechanism 43 including an assembly of satellite rollers 44 is received in the partial cavity 42 and attached to a pump motor (not shown) through a bore (also not shown) formed in the wall 28. In a non-limiting example, the assembly of rollers 44 for the roller mechanism 43 are arranged in a planetary configuration, where each roller 44 is slip-fit onto a respective pin 74 supported by a yoke 76. The yoke 76 is mounted to a drive shaft (not shown), which is operated by the pump motor. As the yoke 76 rotates, the rollers 44 rotate as an assembly. It is to be understood that, since the rollers 44 are slip-fit onto the pins 74, the rollers 44 are also free to rotate individually in response to rotational forces imparted thereto from the rotational movement of the drive shaft.

The mounting pin 14 is coupled to the pump body 12 by disposing the mounting pin 14 on a pump regulator mechanism 82, and operatively disposing the regulator mechanism 82 on the pump body 12. Details of an example of the pump regulator mechanism 82 may be found in U.S. application Ser. No. 11/862,326 filed concurrently herewith, which is commonly owned by the Assignee of the present disclosure, and is incorporated herein by reference in its entirety. Generally, the regulator mechanism 82 allows the mounting pin 14 to slightly move in the y-direction but remains substantially stationary in the x- and z-directions (see FIG. 3). Movement in the y-direction allows the cassette 16, which is mounted to the pump body 12 via the mounting pin 14, to apply a substantially constant force to a flexible tube 68 (shown in FIG. 1), thereby occluding the tube 68 in a relatively consistent manner. It is to be understood that maintaining the mounting pin 14 in a stationary configuration with respect to the x- and z-directions, however, enables the mounting pin 14 to guide the cassette 16 when the cassette 16 is placed or rotated into and/or out of the installed position. This facilitates loading and/or removal of the cassette 16 with the pump body 12, in addition to maintaining the cassette 16 in proper operating position during pumping operation, thereby producing a desirable and suitable pumping performance of the fluid.

In an embodiment, the mounting pin 14 is cylindrically-shaped, has a substantially stout configuration, and is selected from a variety of metals including, but not limited to, aluminum and alloys thereof, steel, stainless steel, zinc and alloys thereof, and combinations thereof. In a non-limiting example, the length of the mounting pin 14 is about equal to the length of a hinge journal 58 (shown in FIG. 3) formed in the cassette 16. As will be described further hereinbelow, the cassette 16 is mounted to the pump body 12 by sliding the hinge journal 58 onto the mounting pin 14 and rotating the cassette 16 into an installed position. The hinge journal/mounting pin configuration provides a desirable bearing surface for the cassette, and facilitates proper alignment of the cassette 16 when installing it in the pump body 12.

Figure 3A:
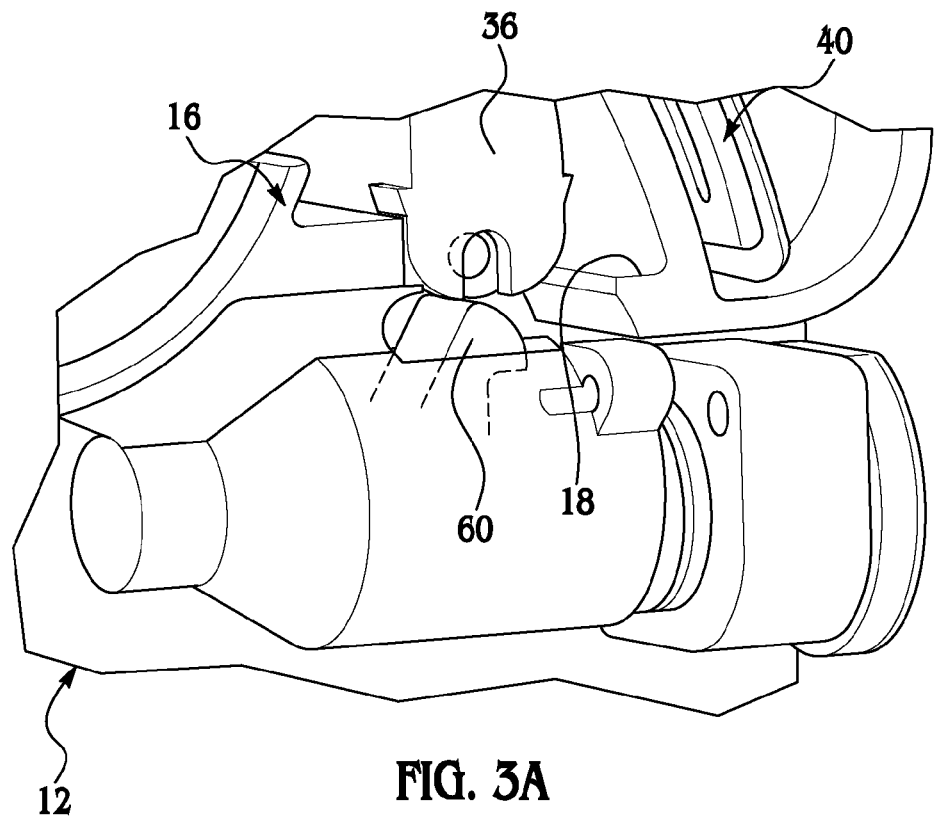
FIG. 3A is a cut-away, enlarged view of a portion of the peristaltic pump assembly of FIG. 3 showing the pump body retaining feature in an opened position.

Without being bound by any theory, it is further believed that the shape and/or conformation of the mounting pin 14, as well as the material(s) selected for the mounting pin 14, contribute to the robustness of the pin 14, which tends to lengthen the usable life thereof. It is to be understood, however, that other shapes and lengths of the mounting pin 14 and/or materials used for the mounting pin 14 may be used and still achieve the desired level of robustness of the pin 14. Formed at the other end 40 of the cassette receiving portion 24 is a pump body retaining feature 60 configured to engage the cassette retaining feature 18 to thereby lock the cassette 16 into the installed position. The retaining feature 60 is generally movable between a closed position (depicted in FIG. 3) and an opened position (depicted in FIG. 3A). As defined herein, the "closed position" refers to either the position of the retaining feature 60 at which the pump body retaining feature 60 engages the cassette retaining feature 18 when the cassette 16 is in the installed position, or refers to the position of the retaining feature 60 towards which the retaining feature 60 biases when the cassette 16 is not in the installed position. Also as defined herein, the "opened position" refers to the position of the retaining feature 60 when the retaining feature 60 is moved away from its biased position (i.e., away from the closed position).

The cassette 16 includes a body 62 including a substantially curved or rounded race 64 disposed between the opposed ends 54, 56 of the cassette 16. An inlet 66 (for the flexible or compressible tube 68) is formed into the body 62 at the first end 54, where the tube 68 fits into a guide member 69. As shown in FIG. 4, the tube 68 extends through the cassette 16, between the cassette body 62 and the pressure sensor 36 and combination pressure/air-in-line sensor 34, and into an outlet 70 formed in the cassette body 62, via another guide member 69. Further details of an example of the cassette 16 may be found in U.S. application Ser. No. 11/862,360 filed concurrently herewith, which is commonly owned by the Assignee of the present disclosure, and is incorporated herein by reference in its entirety.

In an embodiment, the tube 68, which is also disposable, is made of a polymeric material, non-limiting examples of which include silicones, AUTOPRENE (an opaque thermoplastic rubber with high wear resistance derived from SANTOPRENE, commercially available from Advanced Elastomer Systems, a subsidiary of ExxonMobil Chemical located in Houston, Tex.), VITON (a black fluoroelastomer with resistance to concentrated acids, solvents, ozone, radiation and temperatures up to 200° C. with good chemical compatibility, commercially available from DuPont Performance Elastomers located in Wilmington, Del.), TYGON (good chemical resistance with a clear finish, commercially available from Saint-Gobain Performance Plastics Corporation located in Akron, Ohio), PROTHANE II (a transparent, blue, polyester, polyurethane tubing with good chemical resistance, commercially available from Randolph Austin Company located in Manchaca, Tex.), and/or the like, and/or combinations thereof. The inner diameter of the tube 68 may be selected based on the desirable flow rates and the desirable viscosities of the fluid that will flow therethrough. When the cassette 16 is in the installed position, the tube 68 surrounds a portion of the assembly of rollers 44 and abuts the rounded wall 64.

When the pump 10 is operating, rotational movement of the assembly of rollers 44 pumps fluid through the tube 68 to create a pressurized flow thereof. The tube 68 compresses or otherwise occludes at a number of points in contact with the rollers 44 and the rounded race 64 on the other side thereof when the rollers 44, as an assembly and individually, are rotating. Fluid is trapped in the tube 68 between two points of occlusion (i.e., from one roller 44 to an adjacent roller 44). The trapped fluid is passed or moved through the tube 68 at a flow rate proportional to the rotational rate (rpm) of the drive shaft, and released when the tube 68 is no longer occluded by any of the rollers 44. In other words, in response to rotational movement of the rollers 44, portions of the flexible tube 68 that are in contact with the rollers 44 compress or are otherwise occluded against race 64. As a result, fluid is temporarily retained in the tube 68 between the occluded points. In this manner, fluid is urged through the tube 68 via peristaltic wave action.

The hinge journal 58 formed in the cassette body 62 is located at the end 56 of the cassette 16. The hinge journal 58 is generally formed to complement the size and shape of the mounting pin 14 to be received therein. In an embodiment, the hinge journal 58 is cylindrically-shaped and includes a length and diameter that is slightly larger than the mounting pin 14 so that the cylindrically-shaped mounting pin 14 can easily be received therein. Also, the surface of the hinge journal 58 is substantially smooth to facilitate sliding of mounting pin 14 into the hinge journal 58 when the cassette 16 is mounted on the mounting pin 14 and when the cassette 16 is rotated into the installed position.

The cassette retaining feature 18 is formed on the cassette body 62 at the other end 56. The retaining feature 18 is designed to complement or otherwise mate with the retaining feature 60 of the pump body 12. In a non-limiting example, the retaining feature 18 includes a ledge formed into the cassette body 62 and is configured to receive and hold the retaining feature 60 (e.g., a clip) when the retaining feature 60 engages the retaining feature 18.

As disclosed herein, the cassette 16 is placed into the installed position (as shown in FIG. 1) by mounting the cassette 16 to the pump body 12. This is accomplished by sliding the hinge journal 58 formed in the cassette body 62 onto the mounting pin 14. The cassette 16 is thereafter rotated on the mounting pin 14 toward the installed position. As the cassette 16 is rotated, the cassette body 62 enters the cavity 42 of the cassette receiving portion 24, while being guided by the opposed walls 28, 30, the floor, and the mounting pin 14 until the cassette body 62 (including the tube 68) substantially abuts the sensors 34, 36. When the cassette abuts the sensors 34, 36, the retaining feature 18 contacts the retaining feature 60 and the retaining feature 60 moves from the closed position, to the opened position as force is applied thereto. When the retaining feature 18 passes this point of contact, the retaining feature 60 automatically moves back to the closed position. It is to be understood that movement of the retaining feature 60 when the cassette 16 is mounted to the pump body 12 is accomplished by applying a physical force to the cassette 16. The retaining feature 60 momentarily moves to the opened position when the retaining feature 60 is pushed or otherwise forced into the opened position by the cassette 16 as the cassette 16 is placed in the installed position. The retaining feature 60 automatically snaps back into it original position, i.e., the closed position, once the cassette 16 has been placed in the installed position and engages the cassette retaining feature 18, thereby holding or securing the cassette 16 to the pump body 12.

Upon engagement of the pump body retaining feature 60 with the cassette retaining feature 18, the peristaltic pump assembly 10 also provides feedback to the operator or user. The feedback generally indicates that the cassette 16 has been properly assembled with the pump body 12. In a non-limiting example, audible feedback is achieved by a snapping or clicking sound as the retaining feature 60 snaps back into the closed position from the opened position and engages the cassette retaining feature 18 when the cassette 16 is placed in the installed position. This snapping or clicking sound enables the operator to ensure that the cassette 16 has been mounted or otherwise assembled properly, and that pumping of fluid may commence. In another non-limiting example, tactile feedback is achieved when the retaining feature 60 engages the retaining feature 18 and movement of the cassette 16 thereafter cannot occur.

Figure 5:
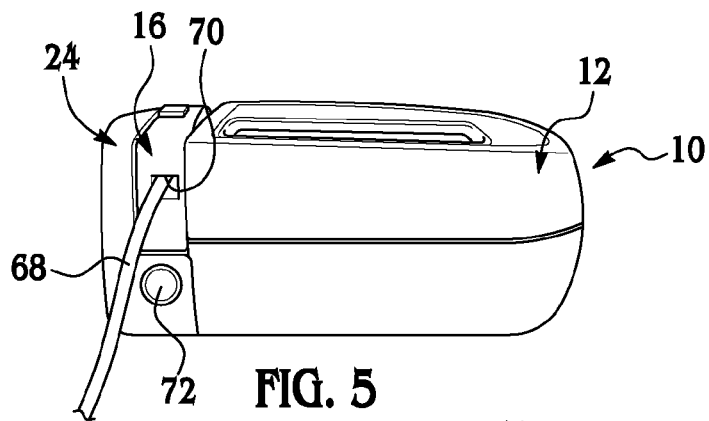
FIG. 5 is an end perspective view of the peristaltic pump assembly of FIG. 1.
Figure 6:
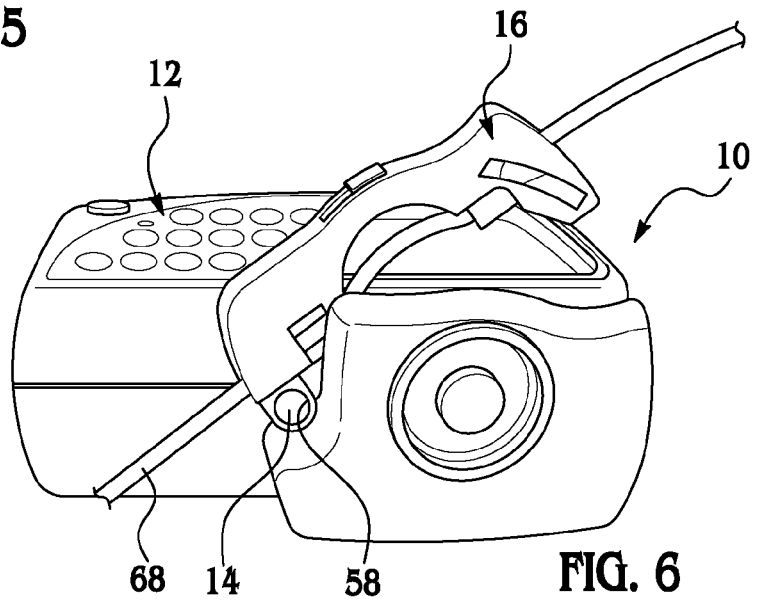
FIG. 6 is a side perspective view of a pump body, showing the cassette out of the installed position.

In an embodiment, and with reference now to FIGS. 5 and 6, the cassette 16 is released from or otherwise rotated out of the installed position by disengaging the pump body retaining feature 60 from the cassette retaining feature 18. Disengagement is achieved when the retaining feature 60 is moved to the opened position, thereby releasing the retaining feature 18. In an embodiment, the retaining feature 60 is moved to the opened position by actuating a release device 72. In a non-limiting example, the release device 72 is a button, whereby when the button is pushed the retaining feature 60 is moved from the closed position to the opened position. The cassette 16 is thereafter rotated about the mounting pin 14 out of the assembled position and slidingly disengaged from the mounting pin 14.

It is to be understood that the term "couple/coupled" or the like is broadly defined herein to encompass a variety of divergent connection arrangements and assembly techniques. These arrangements and techniques include, but are not limited to (1) the direct coupling between one component and another component with no intervening components therebetween; and (2) the coupling of one component and another component with one or more components therebetween, provided that the one component being "coupled to" the other component is somehow operatively coupled to the other component (notwithstanding the presence of one or more additional components therebetween).

While several embodiments have been described in detail, it will be apparent to those skilled in the art that the disclosed embodiments may be modified. Therefore, the foregoing description is to be considered exemplary rather than limiting.

What is claimed is:

1. A peristaltic pump assembly, comprising:
    a pump body;
    a mounting pin coupled to the pump body; and
    a removable cassette having a tube inlet and a tube outlet, said removable cassette slidably received on the mounting pin and secured to the pump body via a retaining feature, wherein the removable cassette is rotatable about the mounting pin;
    wherein the mounting pin is configured to allow the removable cassette to rotate about the mounting pin into an installed position, out of an installed position, or to a position therebetween, said assembly configured to allow movement of the mounting pin relative to the pump body along a linear path that is perpendicular to a straight line between the tube inlet and the tube outlet when the cassette is in the installed position.

2. The peristaltic pump assembly as defined in claim 1 wherein the pump body is configured to guide the cassette as the cassette is rotated into the installed position, out of the installed position, or to the position therebetween.

3. The peristaltic pump assembly as defined in claim 1 wherein the retaining feature comprises a pump body retaining feature included as part of the pump body, which pump body retaining feature is movable between a closed position and an opened position.

4. The peristaltic pump assembly as defined in claim 3 wherein the pump body retaining feature moves from the closed position to the opened position and back to the closed position when the cassette is rotated into the installed position.

5. The peristaltic pump assembly as defined in claim 4 wherein the retaining feature further comprises a cassette retaining feature included as part of the cassette, which cassette retaining feature engages the pump body retaining feature when the pump body retaining feature is in the closed position.

6. The peristaltic pump assembly as defined in claim 5 wherein audible feedback, tactile feedback, or a combination thereof is provided when the pump body retaining feature engages the cassette retaining feature, thereby indicating that the cassette is in the installed position.

7. The peristaltic pump assembly as defined in claim 5 wherein the pump body retaining feature disengages the cassette retaining feature when the pump body retaining feature is in an opened position, and wherein the opened position is achieved by actuating a release device.

8. The peristaltic pump assembly as defined in claim 7 wherein the release device is a button.

9. The peristaltic pump assembly as defined in claim 1 wherein the removable cassette further includes a hinge journal formed therein and configured to slidably receive the mounting pin.

10. The peristaltic pump assembly as defined in claim 9 wherein the hinge journal is formed at an end portion of the removable cassette, and the cassette retaining feature is formed at another end of the cassette.

11. The peristaltic pump assembly as defined in claim 1 wherein the peristaltic pump assembly does not include a door.

* * * * *